United States Patent [19]

Sherwin et al.

[11] 4,045,477

[45] Aug. 30, 1977

[54] ACETOXYLATION PROCESS

[75] Inventors: Martin B. Sherwin, Wayne; I-Der Huang, West Paterson, both of N.J.

[73] Assignee: Chem Systems Inc., New York, N.Y.

[21] Appl. No.: 596,903

[22] Filed: July 17, 1975

[51] Int. Cl.$^2$ .............................................. C07C 67/05
[52] U.S. Cl. ........................ 260/497 R; 260/287 G; 260/295 R; 260/295.5 R; 260/326.13 R; 260/347.5; 260/410.6; 260/465.4; 260/468 R; 260/468 H; 260/469; 260/471 R; 260/473 G; 260/473 S; 260/475 P; 260/476 R; 260/481 R; 260/483; 260/484 R; 260/487; 260/488 J; 260/491
[58] Field of Search ........... 260/497 R, 475 P, 287 G, 260/295 R, 326.13 R, 347.5, 410.6, 465.4, 468, 469, 471 R, 473 G, 476 R, 481 R, 483, 484 R, 487

[56] References Cited

U.S. PATENT DOCUMENTS

| 3,479,395 | 11/1969 | Huguet | 260/497 R |
|---|---|---|---|
| 3,637,515 | 1/1972 | Huguet | 260/497 R |
| 3,668,239 | 6/1972 | Kollar | 260/497 R |
| 3,689,535 | 9/1972 | Kollar | 260/497 R |
| 3,770,813 | 11/1973 | Kollar | 260/497 R |
| 3,872,164 | 4/1975 | Schmidt | 260/497 R |
| 3,907,874 | 9/1975 | Harvey | 260/497 R |

*Primary Examiner*—Lorraine A. Weinberger
*Assistant Examiner*—Michael Shipper
*Attorney, Agent, or Firm*—Bert J. Lewen

[57] ABSTRACT

Vicinal hydroxyesters and diesters are prepared by the oxidation of olefins with molecular oxygen in a carboxylic acid at a temperature of over 150° C. in the presence of a catalyst combination containing tellurium and an iodide source.

10 Claims, No Drawings

ACETOXYLATION PROCESS

This invention relates to the oxidization of olefins to form vicinal hydroxyesters and diesters. More specifically, the invention relates to a specific catalytic process for performing such oxidation at increased yields and selectivity.

In U.S. Pat. No. 3,479,395 issued to Celanese Corporation, it is disclosed that olefins can be oxidized in the liquid phase in the presence of tellurium dioxide at temperatures from 70° to 150° C., preferably from 90° to 100° C. It is proposed that halide ions, preferably chloride ions, benefitted the reaction. Also known in the prior art are the patents to Halcon International, e.g., U.S. Pat. Nos. 3,668,239 and 3,770,813. These patents show the liquid phase oxidation of olefins with catalyst combinations of tellurium and bromine and of a heavy metal of atomic numbers 21–30 and 48 with iodine or an iodide ion.

The aforesaid catalytic processes, while establishing the feasibility of the liquid phase oxidation of olefins, have not produced both rapid reaction rates and high selectivities to the hydroxyesters. The product produced by the previous art is essentially all diester. High selectivity to the hydroxyester is desirable where the mixed esters are to be converted to the corresponding glycol because less acetic acid must be hydrolyzed and dried prior to recycle to the oxidation step. Similarly, the hydroxyesters can be used to produce the corresponding oxirane compounds by a catalytic cracking process described in Belgian Pat. No. 812,109. Vicinal diesters must be hydrolyzed to the hydroxyester prior to cracking. Therefore, a high selectivity to hydroxyester in the olefin oxidation step will reduce the size of the hydrolysis unit.

In accordance with this invention, it has now been discovered that both high reaction rates and selectivities to the hydroxyesters may be obtained by carrying out the reaction in the presence of a tellurium-iodine catalyst system at an elevated temperature, i.e., over 150° C., preferably at least 160° C.

The efficacy of the foregoing catalyst system is particularly surprising in light of the prior art. The Celanese Patent, while mentioning iodine among the possible combinations, shows only work with chlorine in its ten examples, a clear indication that the patentee, if he contemplated iodine, believed it would be inferior. Additionally, and most unexpectedly, applicants have discovered that the temperatures proposed in U.S. Pat. No. 3,479,395 not only are not preferred, but cannot be feasibly used with applicants' catalyst system.

Halcon International's patents further support the unobviousness of applicants' invention. In U.S Pat. No. 3,668,239, the catalyst systems demonstrated in each and every example are restricted to tellurium with bromine. The failure to mention tellurium-iodine is tantamount to a teaching that tellurium-bromine is the best—a finding which applicants unequivocally refute.

That a tellurium-iodine system is unobvious to those skilled in the art is further buttressed by the teaching of Halcon's U.S. Pat. No. 3,770,813. This patent, one attributed to the very same inventor as the prior Halcon patent, shows much work with iodine and iodide, but here combination with tellurium is not suggested. Rather, the disclosure limits the use of iodine to combination with heavy metals having an atomic number of 21 to 30 and 48. (Tellurium's atomic number is 52.)

Other Halcon patents mention tellurium in combination with halogens, but these, too, exemplify bromine. Some also mention chlorine, but there is no reference in these to a catalyst combination of tellurium and iodine. See U.S. Pat. Nos. 3,715,388; 3,715,389; 3,743,672; 3,778,468 and 3,789,065; Canadian Pat. Nos. 882,740; 888,749 and 914,212; and U.K. Pat. No. 1,338,775.

The olefinically unsaturated compounds useful in the process of the invention are preferably the alkenes, ar-alkenes and cycloalkenes. Included among the alkenes are mono-alkenes, di-alkenes and tri-alkenes. The double bond in the mono-alkene may be positioned at any one of the carbon atoms such as alpha, beta, gamma and delta positions and the like. Suitably, these alkenes are straight or branch chain containing from 2 to 30 carbon atoms.

More specifically, the alkenes may be lower alkenes of from 2 to 5 carbon atoms, intermediate alkenes of from 6 to 12 carbon atoms or higher alkenes of from 13 to 30 carbon atoms. The lower alkenes include alkenes such as ethylene, propylene, butene-1, butene-2, 2-methyl-butene-2 and pentene-1. Specific intermediate alkenes are, for example, heptene-2, octene-1, decene-1; and the higher alkenes, such as tetradecene-1, pentadecene-1, hexadecene-1, pentacosene-1, and triacontene-1. Also contemplated are di-alkenes, tri-alkenes, ar-alkenes and cycloalkenes.

Among the di-alkenes the double bond may be conjugated or isolated and the carbon chain may be straight or branched wherein the double bonds are located in any desired position and the olefin may contain up to 30 carbon atoms. The ar-alkenes contemplated by this invention contain an aromatic nucleus with an alkenyl side chain as described above. The cycloalkenes of this invention are compounds containing from 5 to 15 carbon atoms in the nucleus and at least one double bond. Lower di-alkenes may suitably contain up to 8 carbons, the intermediate alkenes 9 to 14 carbons and the higher alkenes 15 to 20 carbon atoms. Examples of these di-lower alkenes are 1,3-butadiene, 1,5-hexadiene, 1,4-pentadiene and 1,3-hexadiene.

More specifically, the ar-alkenes may be ar-lower alkenes such as phenyl alkenes and di-phenylalkenes wherein the alkenyl side chain may be any of those described above. Examples of such compounds are phenyl lower alkenes wherein the alkenes side chain contains from 2 to 5 carbons, such as styrene, 2-methyl styrene and alpha-ethyl-beta-methyl styrene and di-phenyl alkenes such as 1,1-diphenylethylene, 1,2-diphenyl propene and 2,3-diphenyl-but-2-ene.

More specifically, the cycloalkenes may be from 5 to 12 carbon atoms such as cyclopentene, cyclopentadiene, cyclohexene, cyclodecene, and cyclododecene.

All of the above alkenes, ar-alkenes and cycloalkenes may contain one or more functional substituents which are inert to the reaction such as nitro, cyano, chloro, lower alkoxy (methoxy, propoxy), lower alkylthio (methylthio, butylthio) hydroxy, lower alkanoyloxy of 2 to 6 carbons (acetyloxy) and the like.

In the preferred aspects of this invention, the mono- and di-lower alkenes, mono intermediate alkenes, mono higher alkenes, ar-lower alkenes and cycloalkenes are employed; and in the more preferred aspect ethylene, propylene, allyl alcohol, 1,3-butadiene, allyl acetate, allyl chloride, butene-2, methyl butene-2, decene-1, styrene and cyclohexene.

In the most preferred aspects of the invention, ethylene, propylene, butene-2, allyl alcohol, allyl acetate and allyl chloride; but especially ethylene and propylene are the olefinically unsaturated compounds employed in the oxidation to their corresponding hydroxyesters and diesters.

The olefinically unsaturated compound contemplated by this invention may contain the variety of impurities normally associated with commercially available olefins. In addition, it is desirable to employ commercial olefins which contain inert material normally associated with these olefins, such as propane in propylene. Furthermore, these inert materials may be employed in any desired ratio, and preferably used in the various ratios as obtained from a variety of commercial sources.

The carboxylic acid employed in the oxidation supplies the ester moiety to the hydroxyester and diester and is preferably a lower mono-aliphatic acid of from 2 to 6 carbon atoms such as acetic, propionic, butyric, isobutyric, the valeric and caproic acids, as well as their substituted derivatives. Preferably, the substituents are inert under the oxidation conditions. In the preferred embodiments the glycol esters to which the process of this invention is applicable include ethylene and propylene glycol diacetate, dipropionate, dibutyrate, diisobutyrate, divalerates and dicaproates as well as the corresponding mono-esters.

The invention further contemplates the use of intermediate mono-aliphatic acids of from 7 to 12 carbon atoms, such as caprylic, capric and lauric, as well as higher mono-aliphatic acids (of from 12 to 30 carbons) such as myristic, palmitic, stearic, hexacosanoic and tricosanoic. The invention further contemplates the use of substituted mono-aliphatic acids containing one or more functional substituents such as lower alkoxy (methoxy, propoxy), chloro, cyano and lower alkylthio (methylthio, ethylthio, butylthio). Examples are acetoacetic, chloropropionic, cyanoacetic, methoxyacetic acid and 3-methylthiopropionic acid. Among the aromatic acids contemplated are acids containing one or more carboxyl groups such as benzoic, 1-naphthoic, o-toluic, m-toluic, o-chlorobenzoic, m-chlorobenzoic, p-chlorobenzoic, o-nitrobenzoic, m-nitrobenzoic, p-hydroxybenzoic, anthranilic, m-aminobenzoic, p-aminobenzoic, phenylacetic, 2,4-dichlorophenyloxyacetic, hydrocinnamic, 2-phenylbutyric, and phthalic. The alicyclic mono-carboxylic acids may contain from 3 to 6 carbons in the ring, both substituted and unsubstituted, and containing one or more carboxyl groups such as cyclopropanecarboxylic, cyclopentanecarboxylic, and hexahydrobenzoic. The heterocyclic acids may contain from 1 to 3 fused rings both substituted and unsubstituted, containing one more carboxyl groups and containing at least one and less than 4 hetero atoms such as oxygen, sulphur or nitrogen, examples of which may be cited as picolinic, nicotinic, 3-indoleacetic, furoic, 2-thiophenecarboxylic, quinolinic, 2-methylindole-3-acetic, 3-chlorofuroic, and 4-nitronicotinic.

In the more preferred aspects of this invention, the carboxylic acid is an aliphatic acid or aromatic acid, but especially the monophenyl aromatic acids and the lower aliphatic acids such as the lower unsubstituted mono-aliphatic acids or benzoic acid and more especially acetic acid.

The invention further contemplates the use of mixed carboxylic acids in any desired ratio, although it is preferred to employ the same acid as solvent and acid moiety of the subsequently desired ester. It is also within the contemplation of this invention that the final ester product may be used as the solvent. The carboxylic acid employed may suitably be any commercially available acid, such as aqueous acids. It is preferred, however, to employ commercial acids having no more than 15% water, and especially less than 10% water, such as 98% acetic acid. The acid may be recycle acid containing impurities indigenous to the process.

The tellurium metal cation may be provided in its elemental form and added to the oxidation zone as a fine powder or may be added in any form which in solution under oxidation conditions will yield at least some soluble metal ions. For example, the tellurium source may be the carbonate, oxide, hydroxide, iodide, lower alkoxide (methoxide), phenoxide or metal carboxylate wherein the carboxylate ion is the same or different from the solvent anion. In a preferred embodiment, the metal source is its oxide, hydroxide or salt of the acid solvent and, most preferably, the oxide. Furthermore, the tellurium metal compound employed may contain impurities normally associated with the commercially available compounds, and need not be purified any further.

The iodide source used in conjunction with the tellurium compound may be any compound capable of producing iodide ions in solution under the oxidiation conditions. For example, the iodine compound may be $I_2$, hydrogen iodide, a tellurium iodide, an organic iodide or an alkali or alkaline earth metal iodide. Suitable organic iodides include all the derivatives of the olefinically unsaturated compound being oxidized and the reaction products, e.g., olefin iodohydrins, olefin iodo esters and iodo ethers. For example, in the oxidation of ethylene these include 1,2-diiodoethane, ethylene iodohydrin, 2-iodo-ethyl carboxylate and other iodine-containing derivatives of ethylene and including higher molecular weight ethers. Similarly, in the oxidation of propylene, the organic iodides include 1,2-diiodopropane, propylene iodohydrin, 2-iodo-propyl carboxylate and other iodine-containing derivatives of propylene and including higher molecular weight ethers.

The temperatures maintained in the oxidation zone must exceed 150° C. Generally, the temperature is not over 240° C. Temperatures lower than the foregoing lead to inordinately slow reaction rates, while higher temperatures are detrimental to selectivity. However, the temperatures are preferably maintained between about 160° and 190° C.

The total pressure in the oxidation zone should be maintained at from about 50 to about 1000 psia or higher and preferably from about 150 psia to about 400 psia. The pressure must be sufficiently high to maintain the reaction in the liquid phase. Pressures lower than the foregoing result in low reaction rates, while higher pressures, though operable, give no added benefits.

The time of reaction depends to a great extent upon the concentration of reactants and therefore may suitably vary over a wide range. Flow rates are preferably adjusted so that the rate of formation of product as vicinal hydroxyester and vicinal diester is from about 0.10 to 10.0 gram-moles per liter per hour. Once steady state conditions are obtained, the reaction can be continued with anywhere from about 5 to about 60 wt. % of products remaining in the liquid phase reaction medium, but this concentration is preferably maintained at from about 15 to about 50 wt. % based on the total weight of the liquid.

It is normally desired to keep the oxygen concentration of the reactor overhead gas below the flammable range. To do so, oxygen concentration in the feed gas will normally be in the range of 5 to 25 volume %. The oxygen feed gas can be introduced into the liquid separately from the olefin stream. Also inert diluent gases such as $CO_2$, $N_2$, methane and ethane can be allowed to build up in the system to aid in operability outside the flammable region. In general, however, these diluents tend to reduce the reaction rates as they lower the olefin and oxygen partial pressures.

The iodine concentration in the systems feed should be maintained between one half and 15 weight percent with a preferred range of 3 to 8 wt. %. Levels below those cited result in slow reaction rates while levels above those cited lead to inordinate amounts of nonselective products such as alkyl acetates.

Tellurium should be added in amounts related to iodine. The ratio of atoms of iodine to tellurium should be between 1:1 and 20:1 with a range between 4:1 and 14:1 being preferred. Tellurium levels below those cited will lead to low rates and poor selectivities while those levels above those cited will not increase the reaction rate but will increase the amount of high boiling materials, probably ethers, formed in the system.

Water as a product of the reaction will build up in concentration as the reaction proceeds. Concentration levels up to 10 wt. % should be maintained with levels between 0.5 and 5.0 wt. % preferred. Higher water levels lead to significant reductions in reaction rate.

The reaction can be carried out in any device suitable for gas-liquid contacting. Condensate from the cooled overhead gases can be withdrawn from the system or returned to the reactor. Similarly, the reaction can be run with or without the use of mechanical agitators.

The selectivity of the process is extremely high, usually in the region of 95% of theoretical. The products can usually be allowed to build up to a level of up to 60 wt. % in the reactor product. Build-up beyond this level becomes impractical because it leads to low reaction rates due to the diluting effect and high levels of dimerized and trimerized products (heavy ends) which must be recycled to the system.

EXAMPLE 1

Reactions were performed in a 125 ml Fischer-Porter glass reactor equipped with a sparger and a magnetic stirrer. The temperature of the reaction system was maintained by immersing the reactor in a thermostated oil bath at the desired temperature. Nitrogen sparging was used in the oil bath to minimize temperature gradients.

Sevent-five cc of acetic acid along with catalyst were charged to the reactor and brought to and maintained at a temperature of 160° C. The reactant gases, propylene and oxygen, were then sparged at a constant rate of 250 cc/minute to the reactor, the pressure being maintained at 90 ± 5 psia by a Grove regulator. The gas flow was stopped after an hour, the reactor cooled and the contents analyzed via gas chromatography.

Comparative results for several catalyst systems are given below:

TABLE I

| | Catalyst Moles/Liter | Moles/Liter | Moles/Liter Other | Propylene Glycol Acetates Production Rate Moles/Liter-Hour |
|---|---|---|---|---|
| 1. | .04 $TeO_2$ | 0.2 $I_2$ | — | 1.05 |
| 2. | .04 $TeO_2$ | 0.2 $BaI_2$ | — | 1.2 |
| 3. | .04 $TeO_2$ | 0.4 LiI | — | 1.1 |
| 4. | .04 Te | 0.2 $I_2$ | — | 1.1 |
| 5. | .143 $TeO_2$ | — | — | 0 |
| 6. | — | 0.3 $I_2$ | — | trace |
| 7. | .04 $SeO_2$ | 0.2 $I_2$ | .24 $Ba(OAc)_2$ | 0.1 |
| 8. | — | 0.2 $BaI_2$ | .4 $Ba(OAc)_2$ | 0.1 |
| 9. | — | 0.2 $I_2$ | .4 KOAc | 0.2 |

Runs 1 through 4 show the practice of the instant invention. In each and every case, the production rate of the propylene glycol acetate is substantial, namely, in excess of 1 mole per liter-hour. Runs 5 through 9 show that the combination of the two is essential. For example, Runs 5 and 6 show that neither tellurium nor iodine alone is effective. Run 7 shows that selenium is not an effective substitute for tellurium, and unexpected result in light of the close relation of these two metals. Runs 7 and 8 show that combinations of the iodide ion with other metals, namely, barium and potassium, are not useful for catalyzing the reaction.

EXAMPLE 2

Using the equipment and following the procedure described in Example 1, a comparison of the tellurium-iodine and the tellurium bromine system was made with both ethylene and propylene olefin feeds. In the case of ethylene, the gas composition was 10% oxygen and 90% ethylene. The conditions and results are presented in the following table.

TABLE II

| Catalyst Moles/Liter | Moles/Liter | Glycol Acetates Production Rate Moles/Liter-Hour | Mole Ratio Monoacetate/ Diacetate |
|---|---|---|---|
| Propylene | | | |
| 0.2 $I_2$ | .04 $TeO_2$ | 1.1 | 0.62 |
| 0.2 $Br_2$ | .04 $TeO_2$ | 0.6 | 0.40 |
| Ethylene | | | |
| 0.1 $I_2$ | .04 $TeO_2$ | 0.45 | 0.46 |
| 0.1 $Br_2$ | .04 $TeO_2$ | 0.24 | 0.34 |

These data illustrate the significant advantages of the tellurium-iodine combination over the tellurium-bromine combination of the prior art (e.g., U.S. Pat. No. 3,668,239). The rate of reaction is about 85% faster with the iodine system and the hydroxyacetate content of the product is about 35-50% greater. Hydroxyacetate is preferred to diacetate in the product if the material is to be used for glycol production via hydrolysis or for cracking to the corresponding oxirane compound. In the first case less acetic acid must be hydrolyzed and dried prior to recycle, while in the latter case less diacetate must be selectively hydrolyzed to hydroxyacetate before the cracking reaction.

EXAMPLE 3

A reaction was run with a hydrocarbon feed containing 96% isobutylene and 4% butane using the equipment and procedures described in Example 1. The conditions were 80 psia and 160° C. Seventy-five cc of acetic acid along with 0.0031 gram mole of TeO$_2$ and 0.016 gram mole of NaI were charged to the reactor. The gas feed rate was 200 cc/minute of isobutylene and 50 cc/minute of oxygen and was continued for four hours.

At the end of the run the pot contents were analyzed by gas chromatography. They contained 17 wt. % isobutylene glycol monoacetate and 3 wt. % isobutylene glycol diacetate. Other unidentified components, which are believed to be intermediates, accounted for less than 10% of the product.

EXAMPLE 4

Using the reaction system described in Run 1, Example 1 (TeO$_2$/I$_2$), the effect of temperature was studied. The following results were obtained:

| Temperature, ° C. | Propylene Glycol Acetate Production Rate, Moles/Liter-Hour |
|---|---|
| 160 | 1.05 |
| 140 | 0.40 |
| 120 | trace |

This illustrates the uneconomical rates achieved at the temperatures below those claimed. Temperatures above 160° C., requiring higher pressure, could not be run in the glass bottles. The rate of reaction will, however, continue to increase with increased temperatures, as is illustrated in the next example.

EXAMPLE 5

A 1 gallon titanium autoclave fitted with an overhead reflux condenser on the exit line was charged with 1060 grams of 99.5% acetic acid, 50.5 grams of iodine, and 6.7 grams of TeO$_2$. The contents of the autoclave were agitated and brought to 180° C. and 235 psia and a feed of 90 mole % propylene and 10 mole % oxygen was sparged through the reactor at a rate of 8 l./min. for 121 minutes. Analysis of the products at the end of this period showed the following:

| Acetic Acid | 552.7 grams |
|---|---|
| Propylene Glycol | 6.0 grams |
| Propylene Glycol Monoacetate | 235.1 grams |
| Propylene Glycol Diacetate | 361.8 grams |

-continued

| Acetone | 3.4 grams |
|---|---|
| H$_2$O | 32.7 grams |
| Recyclable Intermediates | 64.2 grams |

The production rate of propylene glycol acetates was 2.01 moles per liter per hour. There was no loss of iodine or tellurium from the system. Removal of the product and recycle of the actic acid and intermediates resulted in reaction rates of 2.5 moles per liter per hour and demonstrated a propylene selectivity of above 95 mole %.

We claim:

1. A process for preparing vicinal hydroxycarboxylates and vicinal dicarboxylates which comprises contacting an olefin with molecular oxygen in the liquid phase in the presence of a carboxylic acid at a temperature of at least 160° C. in a reaction zone in the presence of a catalyst of a tellurium metal ion and an iodide source, said carboxylates being the same as the carboxylate group in said carboxylic acid.

2. The process of claim 1 wherein said carboxylic acid has from 2 to 4 carbon atoms.

3. The process of claim 1 wherein the olefin is ethylene, propylene or butylene.

4. The process of claim 1 wherein the tellurium metal ion is introduced into the reaction zone as metallic tellurium, tellurium dioxide, tellurium iodide, tellurium carbonate, tellurium hydroxide or a tellurium carboxylate.

5. The process of claim 1 wherein said iodide source is elemental iodine, hydrogen iodide, an alkaline earth or an alkali metal iodide or an iodo-organic compound.

6. The process of claim 1 wherein the temperature is from 160° to 190° C. and the pressure from 50 to 1000 psia.

7. The process of claim 1 wherein the oxygen concentration in the feed gas ranges from about 5 to 25 volume %.

8. The process of claim 1 wherein the iodide concentration is from 0.5 to 15 weight % and the ratio of atoms of iodide to tellurium is between 1 and 20.

9. The process of claim 1 wherein the iodide concentration is between 3 and 8 weight percent and the ratio of atoms of iodide to tellurium is between 4 and 14.

10. The process of claim 1 wherein the temperature is not greater than about 240° C.

* * * * *